United States Patent [19]

Theeuwes et al.

[11] Patent Number: 5,030,216
[45] Date of Patent: Jul. 9, 1991

[54] OSMOTICALLY DRIVEN SYRINGE

[75] Inventors: Felix Theeuwes, Los Altos; Patrick S. L. Wong, Palo Alto, both of Calif.

[73] Assignee: ALZA Corporation, Palo Alto, Calif.

[21] Appl. No.: 451,476

[22] Filed: Dec. 15, 1989

[51] Int. Cl.$^5$ .............................................. A61K 9/22
[52] U.S. Cl. ................................. 604/892.1; 604/151
[58] Field of Search ............... 604/140, 141, 150, 131, 604/151, 218, 235, 892.1

[56] References Cited

U.S. PATENT DOCUMENTS

| | | | |
|---|---|---|---|
| 3,133,132 | 9/1973 | Theeuwes | 222/95 |
| 3,173,876 | 3/1965 | Zobrist | 252/137 |
| 3,276,586 | 10/1966 | Rosaen | 210/90 |
| 3,541,005 | 11/1970 | Strathmann | 210/19 |
| 3,541,006 | 11/1970 | Bixler et al. | 210/23 |
| 3,546,142 | 12/1970 | Michaeks et al. | 260/2.1 |
| 3,732,865 | 5/1973 | Higuchi et al. | 604/892.1 |
| 3,760,984 | 9/1973 | Theeuwes | 222/95 |
| 3,946,734 | 3/1976 | Dedrick et al. | 604/892.1 |
| 3,971,376 | 7/1976 | Wichterle | 128/260 |
| 3,987,790 | 10/1976 | Eckenhoff et al. | 128/260 |
| 3,995,631 | 12/1976 | Higuchi et al. | 128/260 |
| 3,995,632 | 12/1976 | Nakano et al. | 128/260 |
| 4,320,758 | 3/1982 | Eckenhoff et al. | 604/892.1 |
| 4,327,725 | 5/1982 | Cortese et al. | 128/260 |
| 4,410,328 | 10/1983 | Theeuwes | 604/892 |
| 4,474,575 | 10/1984 | Eckenhoff et al. | 604/131 |
| 4,539,004 | 9/1985 | Eckenhoff et al. | 604/131 |
| 4,723,958 | 2/1988 | Pope et al. | 604/890 |
| 4,838,862 | 6/1989 | Baker et al. | 604/892.1 |
| 4,874,388 | 10/1989 | Wong | 604/892.1 |
| 4,929,233 | 5/1990 | Roth et al. | 604/892.1 |

FOREIGN PATENT DOCUMENTS 2721752 11/1978 Fed. Rep. of Germany ... 604/892.1

Primary Examiner—C. Fred Rosenbaum
Assistant Examiner—Sharon Rose
Attorney, Agent, or Firm—D. Byron Miller; Edward L. Mandell; Steven F. Stone

[57] ABSTRACT

An implantable osmotically driven syringe is disclosed which can be used to deliver a beneficial agent, such as a drug, at a predetermined rate over an extended period of time. A movable piston divides the syringe into a beneficial agent-containing compartment and a driving compartment. The piston is movable into a position wherein the driving compartment has a volume of essentially zero. The syringe is driven by an osmotic engine which has a shaped wall surrounding, and in contact with, an osmotic solute. The wall is comprised of a semipermeable and/or microporous material which is permeable to the external fluid (e.g., water) but is impermeable to the solute. The engine also has a passageway forming a fluid flow path between the osmotic solute and the driving compartment. A portion of the wall is exposed to a fluid-containing external environment. At least about 30% of the wall which contacts the solute also is exposed to the fluid in the external environment. In operation, water from the external environment is imbided through the semipermeable wall forming a solution of the solvent in the osmotic engine. As fresh incoming fluid from the external environment is imbided by the engine, the solution is pumped through the passageway into the driving compartment. The pumping action drives the piston which causes the beneficial agent to be delivered by the syringe.

18 Claims, 2 Drawing Sheets

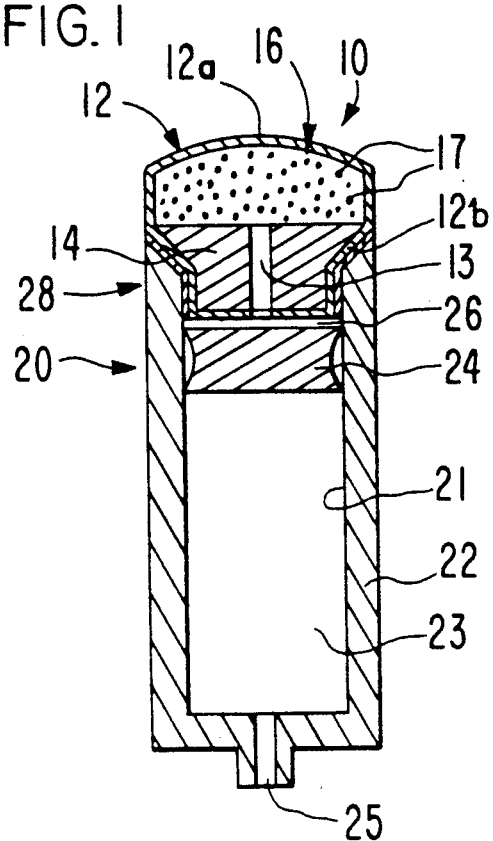
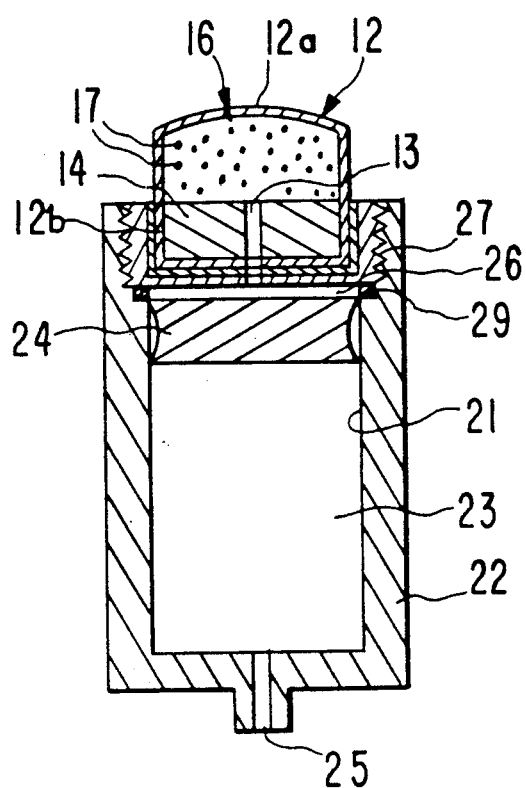
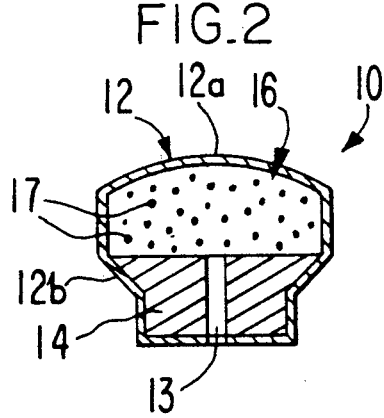
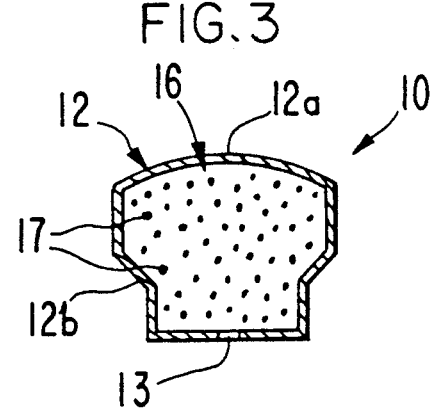
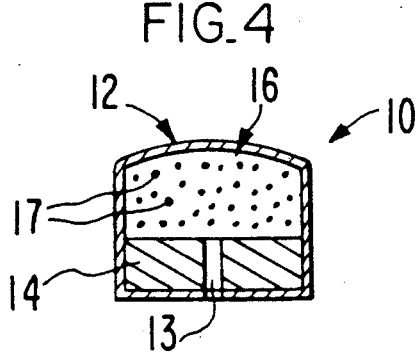

OSMOTICALLY DRIVEN SYRINGE

TECHNICAL FIELD

The invention pertains to a novel and useful osmotically driven syringe and in particular an implantable osmotically driven syringe. The syringe delivers a beneficial agent, such as a drug, to an environment of use, such as an animal body.

BACKGROUND ART

Over the past decade, much research has been devoted to developing new and useful devices for delivering beneficial agents to agent receptor environments of use. For example, in U.S. Pat. No. 3,760,984 issued to Theeuwes, there is disclosed an osmotic delivery device comprising an inner collapsible container carrying on its outer surface a layer of an osmotic solute and a surrounding layer of a polymer permeable to fluid and impermeable to solute. In U.S. Pat. No. 3,971,376 issued to Wichterle, a device is disclosed comprising a capsule having a unitary wall formed of a substantially noncollapsible elastic material that maintains a constant volume and which is adapted to be implanted subcutaneously.

In U.S. Pat. No. 3,987,790 issued to Eckenhoff et al., there is disclosed another osmotic delivery device which contains an outer shape-retaining membrane which surrounds a solute layer which in turn surrounds a collapsible bag containing a liquid drug. Water from the exterior environment permeates through the outer membrane into the solute layer, causing the solute layer to swell The swelling forces the bag to collapse and deliver the drug through a delivery orifice. U.S. Pat. No. 3,995,631 issued to Higuchi et al., discloses a similar device (FIG. 4) comprising an inner flexible bag containing a drug formulation. The bag separates the drug from an osmotically effective solute material. Both the drug and the solute are contained within a housing having an exterior wall that is, at least in part, semipermeable. U.S. Pat. No. 3,995,632 issued to Nakano et al discloses a similar device which incorporates a movable barrier within the housing. The barrier divides the housing into two compartments, one containing the solute and the other containing the drug. The solute-containing compartment has an exterior wall that is, at least in part, semipermeable. The solute-containing compartment acts as an osmotic driver for the device.

U.S. Pat. No. 4,410,328 issued to Theeuwes discloses an osmotically driven pump. The pump includes a housing 11 and a slidable piston 14 which divides the interior of the housing into two compartments. The first compartment contains a liquid drug 13 while the second compartment contains an osmotic driver 17. The osmotic driver is a tablet of an osmotically effective solute, such as sodium chloride, which is coated with a semipermeable wall material. A delivery orifice 20 is drilled through the semipermeable wall. The bottom surface of the osmotic driver 17 is exposed to water from the external environment. This can be done by incorporating a screen, or a plurality of holes through retaining member 18, immediately below the osmotic driver 17. Water from the external environment then contacts and is imbibed through the semipermeable wall 23 into the osmotic driver 17 to form a solution of the osmotic solute. As water continues to be imbibed through the semipermeable wall, the solution in the driver is pumped through delivery orifice 20. The pumped solution eventually fills the space between the osmotic driver 17 and the bottom of piston 14. Thereafter, further pumping of solution from driver 17 forces piston 14 to more forward in housing 11. As the piston moves towards the opening 15, it urges a beneficial agent, such as a drug, out of the compartment 13.

The device illustrated in U.S. Pat. No. 4,410,328 has several potential disadvantages when used as an implantable pump. First, there is a substantial delay between the time when the osmotic driver 17 is exposed to the external aqueous environment (i.e., implanted in the body) and the time when the pump begins dispensing drug. This delay is in part caused by the space surrounding the driver which must first be filled with solution pumped from the driver before the piston is forced to move forward. Secondly, only the bottom surface of osmotic driver 17 is exposed to the external aqueous environment. Because only a relatively small portion (i.e., about 25% or less) of the membrane surface area is exposed to the external aqueous environment, the rate at which water is imbibed through the semipermeable wall 23, and therefore the rate at which the drug is delivered by the pump, is difficult to control. This is especially critical with osmotically driven pumps which are implanted in an animal body. When implanted in certain animal tissues, portions of the external surface of the pump will not be exposed to water. Thus, a dispensing device which utilizes an osmotic engine having only a small surface area of microporous and/or semipermeable membrane exposed will tend to have a greater degree of variability in its drug delivery rate since part or all of the membrane may not be exposed to aqueous body fluids.

While the above-described devices are useful for delivering many agents, and while they represent a valuable contribution to the delivery art, there has been a need in the art for an osmotically driven syringe which begins delivering a drug or other beneficial agent as soon as the syringe is placed in an aqueous environment (i.e., with a minimal lag time between the time when the syringe is placed in the aqueous environment and the time when the syringe begins delivering the beneficial agent).

It is another object of the present invention to provide an osmotically driven syringe which can delivery a beneficial agent, such as a drug, at a more uniform and more predictable delivery rate than was achieved by the osmotically driven syringes of the prior art.

In particular, it is an object of the present invention to provide an osmotically driven syringe having the above-described features and having a size making it suitable for implantation in an animal body and in particular for implantation in a human body.

DISCLOSURE OF THE INVENTION

The present invention provides an osmotically driven dispensing device for delivering a beneficial agent to an environment of use. The device comprises a syringe having a chamber with a movable piston therein, the piston dividing the chamber into a beneficial agent-containing compartment and a driving compartment. The piston is movable into a position wherein the driving compartment has a volume of essentially zero. The device includes an osmotic engine attached to the syringe adjacent the driving compartment. The osmotic engine comprises a shaped wall surrounding, and in contact with, an osmotic solute, an external surface exposed to a fluid in an external environment, and a passageway providing a fluid flow path between the osmotic solute and the driving compartment. The shaped wall is comprised of a material that is permeable to the external fluid and has a sufficient degree of impermeability to the solute to generate an osmotic pressure differential across the wall when exposed to the external fluid. At least about 30% of the wall which is in contact with the osmotic solute is also exposed to the external fluid. Preferably, at least about 50% of the wall which is in contact with the osmotic solute is also exposed to the external fluid. Most preferably, substantially all of the wall which is in contact with the osmotic solute is also exposed to the external fluid.

Preferably, the osmotic engine comprises a shaped wall surrounding a layer of an osmotically effective solute and a layer of a rigid non-dissolving material. The rigid non-dissolving layer provides support for the wall and maintains the wall shape adjacent the driving compartment. The wall preferably comprises a thin membrane that is permeable to the external fluid (e.g., water) and substantially impermeable to the solute. A passageway is provided through both the wall and the rigid non-dissolving layer, thereby providing a fluid flow path between the osmotic solute layer and the driving compartment.

In operation, the external fluid is imbibed through the wall into the osmotic engine forming a solution of the osmotic solute. The solution is pumped through the passageway into the driving compartment as fresh fluid is imbibed through the wall. The pumped solution exerts pressure on the piston, forcing the piston to move within the syringe and deliver the beneficial agent from the beneficial agent-containing compartment to the environment of use.

BRIEF DESCRIPTION OF THE DRAWINGS

FIG. 1 is a cross sectional view of an osmotically driven syringe utilizing a bilayered osmotic engine according to the present invention;

FIG. 2 is an enlarged cross sectional view of the osmotic engine shown in FIG. 1;

FIG. 3 is a cross sectional view of a single layer osmotic engine suitable for use with the syringe illustrated in FIG. 1;

FIG. 4 is a cross sectional view of another embodiment of a bilayered osmotic engine suitable for use according to the present invention;

FIG. 5 is a cross sectional view of the posterior end of an osmotically driven syringe utilizing the bilayered osmotic engine illustrated in FIG. 4;

In the drawings and specification, like parts in related Figures are identified by like numbers.

MODES FOR CARRYING OUT THE INVENTION

Figure 6:
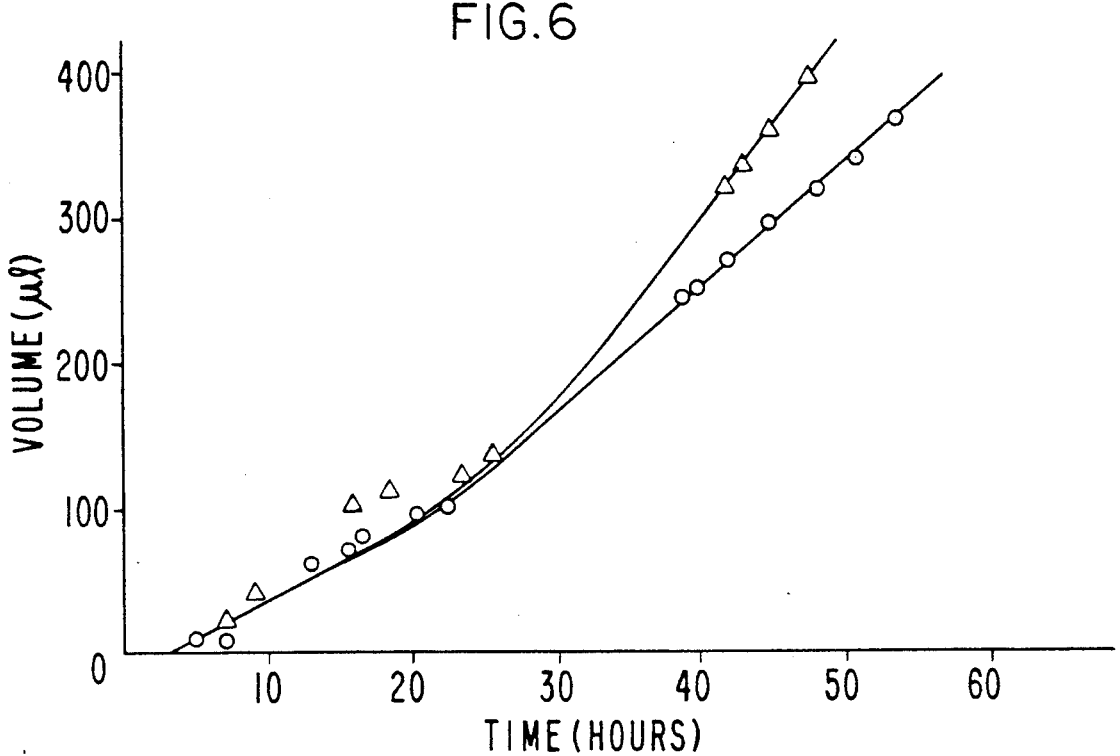
FIG. 6 is a graph showing the volume of a liquid beneficial agent delivered over a period of about 50 hours by an osmotically driven syringe utilizing the osmotic engine illustrated in FIG. 3.

FIG. 1 of the drawings illustrates one example of a new and useful osmotically driven syringe for dispensing a liquid beneficial agent and FIGS. 2-4 illustrate three different embodiments of osmotic engine 10. FIG. 4 illustrates another embodiment of a bilayer osmotic engine which can be used with the syringe illustrated in FIG. 5 having a cylindrically shaped housing.

The osmotic engine is designated in the Figures by the numeral 10. Osmotic engine 10 comprises a semipermeable or microporous wall 12 that encapsulates a tablet 16 of an osmotic agent represented by 17. A passageway 13 through semipermeable wall 12 provides a path for a solution of solute 17 to flow out of osmotic engine 10.

Referring to FIG. 1, the syringe 20 is comprised of a housing 22, which forms an interior chamber 21 having a movable piston 24 therein. The chamber 21 is divided by piston 24 into a beneficial agent-containing compartment 23 and a driving compartment 26. The piston 24 is movable into a position abutting against the engine 10, whereby the driving compartment 26 has a volume of essentially zero and the beneficial agent-containing compartment 23 has a maximum volume.

The initial zero volume feature of compartment 26 has several benefits. First, the lag time for the syringe 20 to begin pumping the beneficial agent from compartment 23 is minimized. This feature is important in those instances where it is desired to have syringe 20 begin delivering beneficial agent as soon as possible after the syringe 20 is placed in the fluid containing environment of use. The prior art osmotically driven pumps, such as the one disclosed in U.S. Pat. No. 4,410,328 typically had an initial lag period on the order of about 10 to about 15 hours depending upon the size of the pump. In the osmotically driven syringe of the present invention, the lag period has been reduced by about 70% thereby providing a lag period of only about 3 to about 5 hours for equivalently sized pumps/syringes. Second, compartment 26 contains substantially no air. This is desirable because any air initially trapped in compartment 26 will cause a certain amount of pressure fluctuation on the piston 24 once osmotic engine 10 begins pumping solution. These pressure fluctuations cause variations in the delivery rate of syringe 20. Third, air initially trapped within chamber 26 creates a potential hazard in intravenous drug delivery applications since the trapped air can leak into the beneficial agent-containing compartment 23. In the present invention, this potential hazard is eliminated.

Syringe 20 also has a delivery port 25 which can be shaped to accept a hypodermic needle, an IV catheter or the like. Piston 24 fits snugly against the internal surface of housing 22 and forms a fluid tight seal between compartment 23 and compartment 26. Piston 24 may be made of rubber, nylon, polytetrafluoroethylene and the like. Likewise, the housing 22 may be made from well known materials such as metals or plastics that are inert relative to the liquids they contact and are nonirritating to an animal body. Examples of suitable materials include stainless steel, aluminum, polyolefins such as polypropylene and polyethylene, polyesters, polyamides, and polycarbonates. Of these, polypropylene is preferred.

The osmotic engine 10 is sealed within the posterior end portion 28 of syringe 20. The interior surface of end portion 28 is bevelled as shown in FIG. 1. The osmotic engines 10 illustrated in FIG. 2 and 3 are correspondingly shaped to closely fit against the bevelled surface of end portion 28 and form a fluid tight seal therewith.

Of course, it is within the scope of the present invention to utilize a syringe housing having other shapes. For instance, the interior surface of end portion 28 may be cylindrically shaped with no bevelling. As shown in FIG. 5, the interior surface of end portion 28 is threaded and adapted to receive a threaded cap 27. The inner surface of cap 27 is cylindrically shaped to receive an osmotic engine 10 as shown in FIG. 4 with the outer diameter of engine 10 closely approximating the inner diameter of cap 27. The osmotic engine 10 may be secured within cap 17 using an adhesive. An O-ring 29 may optionally be provided to ensure a fluid tight seal between cap 27 and syringe housing 22. Cap 27 may be made from the materials used to make housing 22 or the materials used to make membrane 12. Preferably, cap 27 is made from polystyrene, polyvinylchloride, polyacetal, polymethyl methacrylate, cellulose acetate or cellulose acetate butyrate.

The osmotic engine 10 may be secured to the end portion 28 of syringe 20 (or to cap 27) by conventional means. For example, the osmotic engine 10 may be attached to housing 22 (or to cap 27) using an adhesive which can adhere to the material used to construct the syringe (typically plastic) and the material used to form the semipermeable wall 12 (typically a cellulosic polymer). When utilizing a plastic housing 22 (or a plastic cap 27) and a cellulosic wall 12, pharmaceutically acceptable acrylic-based adhesives are preferably used. It is important to orient osmotic engine 10 with the passageway 13 opening into compartment 26.

Wall 12 is preferably comprised of a membrane that possesses permeability to an external fluid such as water while simultaneously possessing some degree of impermeability to osmotic agent 17, typically a salt or sugar. Wall 12 can be formed of a semipermeable material that has uniform properties across all its dimensions, that is, it is substantially imperforate or substantially homogenous. Alternatively, wall 12 can be formed of a microporous material, that is, a material having micropores or microholes. Furthermore, wall 12 can be formed of a material that is both semipermeable and microporous, allowing an external fluid to permeate through while remaining substantially impermeable to osmotic agent 17. When wall 12 is comprised of a material that is substantially imperforate, molecules of the external fluid dissolve in and diffuse through wall 12 and into engine 10. When wall 12 is comprised of a microporous material, molecules of the external fluid migrate and diffuse into the micropores, then into engine 10. When wall 12 is comprised of a material having both of these properties, external fluid enters engine 10 by a concurrent operation of each of these mechanisms, that is, by osmosis through wall 12 and by diffusion through the pores of wall 12.

As shown in FIGS. 1 and 5, a portion of wall 12, the portion designated 12a, is exposed to the external environment while a second portion of wall 12, designated 12b, is sealed within the syringe housing 22 and thus is not exposed to the external environment. As is clearly shown in FIGS. 1 and 5, the interior surfaces of wall portion 12a are in contact with the tablet 16 of osmotic agent 17. In the most preferred embodiments illustrated in FIGS. 1 and 5, substantially all of the wall portion 12a which is exposed to the external fluid is also in contact with the osmotic agent 17. However, it is also within the scope of the present invention to utilize an osmotic engine in which at least 30% of the wall portion which is in contact with the osmotic solute along its interior surface is also exposed to the external environment along its exterior surface. More preferably, at least about 50% of the wall portion which is in contact with the osmotic solute along its interior surface is also exposed to the external environment along its exterior surface. By maximizing the wall surface area exposed to the external environment, the variability in the pumping rate of osmotic engine 10 is reduced.

Preferably, as shown in FIGS. 1, 2 and 4, the osmotic engine has a bilayered configuration including a layer of an osmotic agent 17 and a second layer 14 comprised of a rigid non-dissolving material. The layer 14 may be comprised of any rigid, non-dissolving material such as rigid plastics, ceramics, glasses and/or metals. Preferably, layer 14 is comprised of a sterilizable, inert material. Most preferably, layer 14 is comprised of a powdered material that becomes rigid after compression. Examples of non-dissolving powdered materials that become rigid after compression include powdered micropolyethylene wax and powdered calcium diphosphate. Generally, because the material forming layer 14 is non-dissolving, it will have little or no osmotic activity. In the most preferred embodiments shown in FIGS. 1 and 5, the wall portion 12b has an interior surface that is in direct contact with layer 14 and not in direct contact with agent 17. On the other hand, substantially all of the wall portion 12a has an interior surface which is in contact with the osmotic agent 17. Thus in the most preferred embodiments illustrated in FIGS. 1 and 5, substantially all portions of wall 12 having an osmotic concentration gradient there-across, are also exposed to the exterior environment.

In the embodiment illustrated in FIG. 3, the osmotic engine 10 has a single layer configuration. The osmotic agent 17, optionally mixed with binders and/or buffers, is compressed to form a tablet 16. The compression step may be performed in a conventional tablet making machine. The tablet 16 is then coated with a solution of a suitable semipermeable/microporous film forming material in accordance with known methods to form the semipermeable/microporous wall 12. Lastly, the passageway 13 is drilled into one side of osmotic engine 10 using a drill, laser or other known technique.

The bilayered osmotic engine 10 illustrated in FIGS. 1, 2, 4 and 5, may be formed by concurrently compressing a layer of a suitable osmotic agent 17, optionally mixed with binders and/or buffers, and a layer 14 of a non-dissolving material which hardens upon compression. The compression step may be conducted in a conventional tablet making machine to form the bilayered tablet 16 having the structures illustrated in FIGS. 2 and 4. The bilayered tablet 16 is then coated with a solution of a suitable semipermeable/microporous film forming material in accordance with known methods to form the semipermeable/microporous wall 12. Lastly, the passageway 13 is drilled into one side of osmotic engine 10 using a drill, laser or other known technique. When drilling a bilayered tablet 16, the passageway 13 is drilled in the side of the tablet 16 having the rigid non-dissolving layer 14. It is important to drill the passageway 13 completely through layer 14 in order to provide an open fluid flow path which enables the solution of osmotic agent 17 to be pumped through passageway 13 to the driving compartment 26 of the syringe 20.

Because layer 14 is composed of a rigid non-dissolving material, its structural integrity is not affected by the pumping of fluid through osmotic engine 10. As the agent 17 within osmotic engine 10 is dissolved, the layer 14 provides a rigid structural support for the wall portion 12b which is attached to syringe 20. Thus, even as the active agent 17 is dissolved and pumped out of engine 10, the layer 14 retains its original shape and therefore wall portion 12b remains sealed to syringe 20.

Typical materials for forming wall 12 include synthetic or naturally occurring semipermeable and/or microporous membranes known to the art as osmosis and reverse osmosis membranes. Preferably, wall 12 is comprised of a cellulose ester. Examples of suitable membrane materials include commercially available unplasticized cellulose acetate, plasticized cellulose acetate, reinforced cellulose acetate, cellulose nitrate with 11% nitrogen, cellulose diacetate, cellulose triacetate, agar acetate, amylose triacetate, beta glucan acetate, beta glucan triacetate, cellulose acetate, acetaldehyde dimethyl acetate, cellulose acetate ethyl carbamate, cellulose acetate phthalate, cellulose acetate methyl carbamate, cellulose acetate succinate, cellulose acetate dimethaminoacetate, cellulose acetate ethyl carbonate, cellulose acetate chloroacetate, cellulose acetate ethyl oxalate, cellulose acetate methyl sulfonate, cellulose acetate butyl sulfonate, cellulose acetate propionate, cellulose acetate p-toluene sulfonate, triacetate of locust gum bean, cellulose acetate with acetylated hydroxyethyl cellulose, hydroxylated ethylene-vinylacetate, cellulose acetate butyrate having a viscosity of from about 10 seconds to about 50 seconds, cellulose acetate butyrate containing about 17 percent of combined butyryl and about 29.5 percent acetyl, cellulose acylate, cellulose diacylate, cellulose triacylate, permselective, aromatic nitrogen-containing polymeric membranes that exhibit water permeability and essentially no solute passage, osmosis membranes made from polymeric epoxides, osmosis membranes made from copolymers of an alkylene oxide and alkyl glycidyl ether, semipermeable polyurethanes, semipermeable polyglycolic or polylactic acid and derivatives thereof, thin film membranes as disclosed by Loeb and Sourirajan in U.S. Pat. No. 3,133,132, the membranes of ionically associated polyelectrolytes, the polymers formed by the co-precipitation of polycation and a polyanion as described in U.S. Pat. No. 3,276,586; 3,541,005; 3,541,006; 3,546,142; 3,173,876; derivatives of polystyrene such as poly(sodium styrenesulfonate) and poly(vinylbenzyl-trimethyl-ammonium chloride), and the like. Wall 12 may also be formed from a microporous membrane such as polysulphone, polyvinyl chloride, polystyrene, nylon, polycarbonate, polymethyl methacrylate, and other materials using soluble pore forming agents. Generally, membranes having an osmotic fluid permeability of $10^{-5}$ to $10^{-9}$ cm$^2$/atm/hr against a saturated solute solution at the temperature of use while simultaneously possessing a sufficient degree of impermeability to the solute to generate an osmotic pressure differential across the membrane are useful and within the spirit of the invention.

Semipermeable wall 12 may also contain a wall forming pharmaceutically acceptable polymer or agent which acts as a permeability enhancer to aid the passage of fluid into the osmotic engine 10. Representative of polymers and agents for the present purpose include water soluble and/or swellable polymers such as hydroxypropyl cellulose, hydroxypropyl methylcellulose, hydroxyethyl cellulose, ethyl methylcellulose, methylcellulose, acrylics including polyacrylic acid, polyethyl methacrylate, polymethyl methacrylate, pyrrolidones including polyvinyl pyrrolidone, alkylated vinylpyrrolidone polymers, poly(vinylpyrrolidone/vinyl acetate) copolymers, vinylpyrrolidone/dimethylamino-ethylmethacrylate copolymers, maleic acid polymers such as monobutyl ester of poly(methyl vinylether/maleic acid), monoethyl ester of poly(methylvinyl ether/maleic acid), poly(methylvinylether/maleic anhydride) copolymer, polyvinyl alcohol hydrolyzed 75 to 85%, water soluble agents such as polyethylene glycol, polyethylene oxide, guar gum, gum arabic, dextran, citric acid, triethyl citrate, acetyltriethyl citrate, sucrose, fructose, glycerin, triacetin, and the like.

Various osmotically effective solutes which can be used as the osmotic agent 17 include solutes and hydrophilic polymers. Suitable hydrophilic polymers include those described in U.S. Pat. No. 4,327,725. Suitable solutes include magnesium chloride, sodium chloride, lithium chloride, potassium chloride, potassium sulfate, sodium carbonate, sodium sulfite, lithium sulfate, calcium bicarbonate, sodium sulfate, calcium sulfate, potassium acid phosphate, calcium lactate, magnesium succinate, tartaric acid, soluble carbohydrates such as raffinose, glucose, lactose, mixtures thereof and the like. Of these, sodium chloride, potassium chloride, glucose and lactose are preferred. The solid solute can be in any suitable physical form such as particles, crystals, pellets, tablets, strips, film, granules and the like. However, from a manufacturing standpoint, the osmotic agent 17 is preferably first compressed into a solid tablet, either as a homogenous single layer tablet or with a second layer 14 comprised of a rigid, non-dissolving material, prior to coating with the semipermeable membrane material.

The rate of liquid (e.g., water) influx per unit area of semipermeable membrane will depend upon the composition and thickness of the membrane and the magnitude of the osmotic imbalance (this assumes insignificant back pressure from the piston 24). In syringes that are used to administer a drug intravenously, the osmotic pressure of the solute solution must exceed the blood pressure of the animal (about 10 kPa in humans). Sodium chloride is an especially effective osmotic solute in that the osmotic pressure of sodium chloride is sufficiently high to remove the dependence of pumping rate on the osmotic pressure of the surrounding environment. By keeping the osmotic imbalance substantially constant, the influx of liquid into osmotic engine 10 will be constant and so will both: (1) the rate of delivery of solution from osmotic engine 10 into compartment 26, and (2) the rate of delivery of the beneficial agent from compartment 23. Such operation is called "steady state" or "tonic" operation and is characterized by a controlled constant rate of delivery at a predetermined baseline level.

In operation, the syringe 20 may be filled with a suitable beneficial agent by moving piston 24 with a plunger (not shown), thereby filling compartment 23 with a suitable dose of the beneficial agent. Agents that can be dispensed by syringe 20 include a wide range of drugs, antibacterials, antifungals, plant growth promoters, surfactants, chemical reactants, and the like. It is within the scope of the present invention to utilize a syringe 20 which has been prefilled with a dose of a liquid beneficial agent or which is filled by the patient using a plunger which can be easily connected to piston 24 for drawing the dosage and which is easily disconnected from piston 24 once the appropriate dosage has been drawn.

Next, a suitable osmotic engine 10 is sealed within the end portion 28 of syringe 20. Those skilled in the art will appreciate that the osmotic engine 10 can be selected to deliver beneficial agent at a predetermined pumping rate. The pumping rate of osmotic engine 10 can be varied, as is known in the art, by varying (1) the composition of osmotic agent 17, (2) the composition of wall 12 and (3) the surface area of wall portion 12a exposed to the exterior aqueous environment.

The thus assembled syringe 20 may then be placed in an aqueous environment wherein the wall portion 12a is exposed to water. Water from the aqueous environment is imbibed through the wall portion 12a into osmotic engine 10 where it forms a solution of the osmotic agent 17. The imbibition of liquid, from either a fluid reservoir or an external environment such as an animal body, through wall portion 12a and into engine 10 is caused by an osmotic imbalance between the liquid and the composition of osmotic agent 17. As fresh liquid is imbibed through wall portion 12a, the solution of osmotic agent 17 is "pumped" through passageway 13 and into the compartment 26. The pumping of solution from osmotic engine 10 forces piston 24 to move toward delivery port 25, thereby forcing the beneficial agent out of port 25.

Alternatively, if the syringe 20 is to be used in a nonaqueous environment, for example as a portable nonimplantable pump worn outside the body, a fluid reservoir container (not shown in the figures) may be attached to the end portion 28 of syringe 20 by conventional fastening means (e.g., screw threads) for supplying the necessary fluid needed to run the osmotic engine 10. When the reservoir container is fastened to end portion 28, the semipermeable wall portion 12a of osmotic engine 10 is exposed to the fluid. The fluid reservoir container may also contain a wicking material, such as a hydrogel or a sponge, which maintains the wall portion 12a continuously wetted by the reservoir fluid, regardless of the movement or physical orientation of the syringe/reservoir assembly. The thus assembled syringe 20/reservoir may be secured, for example using straps or tape, on the patient with a needle or catheter (not shown) penetrating the cutaneous layer. Alternatively, the needle can be inserted into a vein and the syringe utilized as an IV infusion device.

Alternatively, the fluid in compartment 23 may be inert and the syringe 20 may be used simply as a displacement pump. In this embodiment the syringe 20 must be suitably interconnected by well known means to a reservoir of a fluid beneficial agent to be discharged, such that the inert fluid displaces the beneficial agent from the reservoir in a predetermined regimen to the desired administration site. Such alternatives ar particularly attractive in instances in which the beneficial agent is incompatible with housing 22.

The osmotically driven syringe of the present invention may be used to deliver dosages having a fluid volume in a range of about 0.2 to about 20 cm$^3$ over a period of about 0.5 to about 15 days. Preferably, the syringe 20 has a size suitable for implanting in a human or other animal body. Implantable syringes have a compartment 23 which can typically hold from about 0.2 to 10 cm$^3$ of a liquid beneficial agent. The osmotic engines useful in the osmotically driven syringe disclosed herein typically provide a delivery rate of about 0.1 to about 40 cm$^3$/day.

The osmotically driven syringe 20 described herein is particularly useful for the long-term administration of polypeptides such as insulin and buserelin, analgesics such as morphine sulfate, hydromorphone HCl, oxymorphone HCl, methadone HCl; anti-psychotics such as dihydroergotamine mesylate and promethazine HCl; anti-asthmatics such as aminophylline and terbutaline sulfate; anti-thrombotic agents such as heparin Na, urokinase and streptokinase; hormones such as corticotropin; anti-nausea agents such as metoclopramide HCl; anti-cancer drugs such as bleomycin sulfate, adriamycin, 5-fluorouracil and 5-fluorouracil deoxyribose; antibiotics such as polymyxin B and amphotericin B; ion chelating agents such as deferoxamine mesylate; narcotic antagonists such as naloxone HCl; and ritodrine HCl.

Syringe 20 can be made as a disposable device for delivering a single dose of a beneficial agent. Alternatively, syringe 20 can be made as a reusable device. That is, agent compartment 23 can be refilled, osmotic engine 10 can be replaced with another engine having the same or a different pumping rate, and in the case of a nonimplantable pump, the fluid reservoir container can be refilled to ensure a continuous supply of the external fluid.

Having thus generally described the invention, the following examples will further illustrate preferred embodiments thereof.

EXAMPLE 1

A standard 1 ml polypropylene syringe having a silicone rubber plunger was modified by beveling the interior surface of the posterior end of the syringe housing to the configuration shown in FIG. 1. Two similar osmotic engines were constructed. Each engine was formed by compressing 350 mg of powdered NaCl in a standard tablet making machine. The compressed salt tablet had the shape of tablet 16 illustrated in FIG. 3 with a (largest) diameter of about 9 mm and a height of about 4 mm. The tablet was then spray coated with a solution of cellulose acetate in methylene chloride and methanol solvent. The coated tablet was then placed in an oven maintained at 50° C. for a period of 24 hours to evaporate off the residual solvent. The resulting membrane coating had a wall thickness of about 7 mils. A 25 mil fluid delivery passageway was drilled through the membrane wall. The osmotic engine was fastened to the bevelled posterior end of the syringe using an acrylic-based adhesive.

The agent-containing compartment was filled with water. With the agent-containing compartment filled, the plunger abutted against the osmotic engine and the driving compartment had substantially zero volume. A catheter was fastened to the delivery port of the syringe with the free end of the catheter leading to an empty graduated cylinder. The entire syringe was then submerged in water and the pumping of water from the syringe into the graduated cylinder was monitored over a period of about 2 days. The volumetric fluid delivery profile of the syringe with each of the two osmotic engines was monitored over a period of about 2 days. The data is plotted in FIG. 6. The syringe began pumping water about 3 hours after being submerged. Because the osmotic engine had no rigid non-dissolving support layer (i.e., the engine had the configuration illustrated in FIG. 3), the portions of the membrane surface area which were exposed to external water tended to expand slightly during operation, resulting in a slight increase in the delivery rate after about 30 hours.

EXAMPLE 2

The syringe used in Example 1 was tested with two similar osmotic engines having a bilayered configuration as shown in FIG. 2. Each of the osmotic engines was formed by concurrently compressing a layer containing 175 mg of powdered micropolyethylene wax (Fischer-Tropsch wax having a particle size in the range of 1-3 um) and a layer containing 175 mg of NaCl. Upon compression, the micropolyethylene wax layer became hardened. The compressed bilayered tablet was then coated with a solution of cellulose acetate and dried in accordance with the procedures described above in Example 1. The membrane wall had a thickness of about 7 mils. A 25 mil fluid delivery passageway was drilled through the membrane wall and the polyethylene wax layer. The osmotic engine was then fastened to the bevelled posterior end of the syringe using an acrylic-based adhesive.

Figure 7:
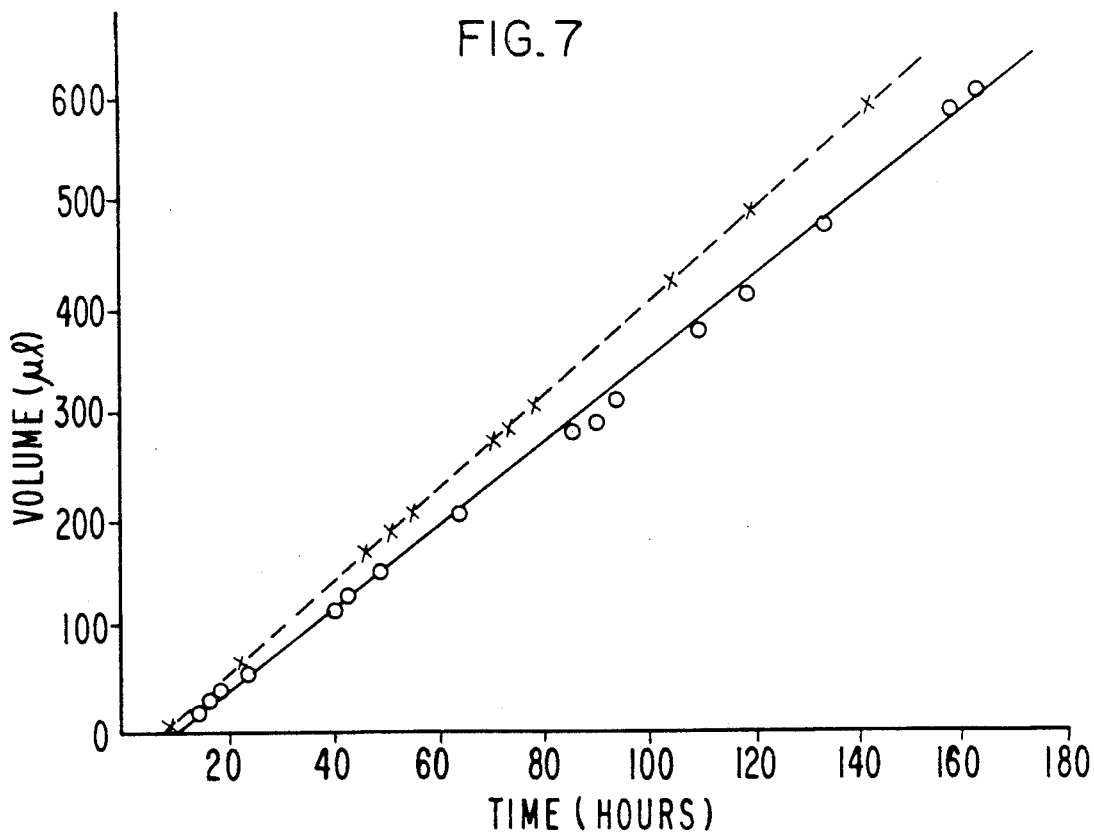
FIG. 7 is a graph showing the volume of a liquid beneficial agent delivered over a period of about 160 hours by an osmotically driven syringe utilizing the osmotic engine illustrated in FIG. 2.

The fluid delivery profile of the syringe was then tested in accordance with the same procedures described above in Example 1. The volumetric fluid delivery profile of the syringe with each of the two osmotic engines was monitored over a period of about seven days. The data is plotted in FIG. 7. The syringe began pumping water about 10 hours after being submerged. The delay period (10 hours) for this engine was longer than the delay period (3 hours) for the engine tested in Example 1. The longer delay was due in part to the lower pumping rate for this engine. Because the engine had a rigid non-dissolving internal support layer, the membrane surface area which was exposed to the external water was maintained substantially constant (i.e., no expansion of the membrane) resulting in a more uniform pumping rate as shown in FIG. 7.

While certain preferred embodiments of the present have been selected for illustration in the drawings and have been described in detail herein, the illustrated embodiments should not be construed as limiting and those skilled in the art will appreciate that various modifications, changes and additions to the illustrated embodiments may be made without departing from the spirit and scope of the present invention as defined in the appended claims.

We claim:

1. An osmotically driven dispensing device for delivering a beneficial agent to an environment of use, the device comprising:
    a) a syringe having a chamber with a movable piston therein, the piston dividing the chamber into a beneficial agent-containing compartment and a driving compartment, the piston being movable into a position wherein the piston occupies substantially all of the drive compartment;
    b) an osmotic engine attached to the syringe adjacent the driving compartment, the engine comprising a shaped wall surrounding, and in contact with, an osmotic solute, the wall having an external surface exposed to a fluid in an external environment, and a passageway providing a fluid flow path between the osmotic solute and the driving compartment, the wall being comprised of a material that is permeable to the external fluid and having a sufficient degree of impermeability to the solute to generate an osmotic pressure differential across the wall when exposed to the external fluid, at least 30% of the wall which is in contact with the osmotic solute also being exposed to the external environment;
    wherein in operation, the external fluid is imbibed through the wall into the osmotic engine to form a solution of the osmotic solute, the solution being pumped through the passageway into the driving compartment as fresh fluid is imbibed through the wall, thereby exerting pressure on the piston and forcing the piston to move within the syringe chamber and deliver the beneficial agent from the beneficial agent-containing compartment to the environment of use.

2. The device of claim 1, wherein the osmotic engine comprises a shaped wall surrounding a layer of an osmotically effective solute, the shaped wall also surrounding a layer of a rigid, non-dissolving material, the rigid material providing a rigid support for the shaped wall in order to fixedly attach the osmotic engine to the syringe.

3. The device of claim 2, wherein the passageway extends through both the wall and the rigid, non-dissolving layer to provide a fluid flow path between the osmotic solute and the driving compartment.

4. The device of claim 2, wherein the rigid, non-dissolving layer is comprised of a material selected from the group consisting of rigid plastics, metals, ceramics and glasses.

5. The device of claim 4, wherein the rigid, non-dissolving layer is comprised of micropolyethylene wax.

6. The device of claim 1, wherein the syringe is comprised of plastic.

7. The device of claim 6, wherein the plastic comprises polypropylene.

8. The device of claim 1, wherein the semipermeable wall material is comprised of a cellulose ester.

9. The device of claim 1, wherein the cellulose ester is selected from the group consisting of cellulose acetate and cellulose acetate butyrate.

10. The device of claim 1, wherein the external fluid comprises water.

11. The device of claim 1, wherein the osmotically effective solute is selected from the group consisting of sodium chloride, potassium chloride, glucose, lactose and hydrophilic polymers.

12. The device of claim 1, wherein the osmotic engine is adhered to the syringe.

13. The device of claim 12, wherein the osmotic engine is adhered to the syringe using an acrylic-based adhesive.

14. The device of claim 1, wherein at least 50% of the wall which is in contact with the osmotic solute is also exposed to the external environment.

15. The device of claim 1, wherein substantially all of the wall which is in contact with the osmotic solute is also exposed to the external environment.

16. The device of claim 1, wherein the beneficial agent-containing compartment contains a liquid beneficial agent.

17. The device of claim 1, wherein the beneficial agent-containing compartment has a maximum volume when the volume of the driving compartment is essentially zero.

18. The device of claim 1, wherein the environment of use is within an animal body.

* * * * *

UNITED STATES PATENT AND TRADEMARK OFFICE
CERTIFICATE OF CORRECTION

PATENT NO.  : 5,030,216
DATED       : Jul. 9, 1991
INVENTOR(S) : Felix Theeuwes and Patrick S.L. Wong It is certified that error appears in the above-identified patent and that said Letters Patent is hereby corrected as shown below:

Title Page:
   In item ]57], Abstract, lines 20 and 23, "imbided" should read --imbibed--.

Column 11, line 49, "drive" should read --driving--.

Signed and Sealed this

Seventeenth Day of November, 1992

Attest:

DOUGLAS B. COMER

*Attesting Officer*   Acting Commissioner of Patents and Trademarks